United States Patent
Walz et al.

(10) Patent No.: US 6,734,223 B2
(45) Date of Patent: May 11, 2004

(54) POLYAMINOESTER AND THEIR APPLICATION IN DENTAL COMPOSITIONS

(75) Inventors: Uwe Walz, Konstanz (DE); Joachim E. Klee, Radolfzell (DE)

(73) Assignee: Dentsply DeTrey GmbH (DE)

( * ) Notice: Subject to any disclaimer, the term of this patent is extended or adjusted under 35 U.S.C. 154(b) by 0 days.

(21) Appl. No.: 09/925,174

(22) Filed: Aug. 9, 2001

(65) Prior Publication Data

US 2002/0045677 A1 Apr. 18, 2002

Related U.S. Application Data

(60) Provisional application No. 60/224,669, filed on Aug. 11, 2000.

(51) Int. Cl.$^7$ ............................ A61K 6/08; A61K 31/74
(52) U.S. Cl. ..................... 523/116; 523/118; 424/78.1
(58) Field of Search ................................. 523/115, 105, 523/109, 116, 118; 564/511, 512; 106/35; 424/78.1; 562/553, 561

(56) References Cited

U.S. PATENT DOCUMENTS

| | | | |
|---|---|---|---|
| 4,089,763 A | 5/1978 | Dart et al. | 204/159.23 |
| 4,297,266 A | 10/1981 | Ibsen et al. | 260/42.14 |
| 4,323,348 A | 4/1982 | Schmitz-Josten et al. | 433/228 |
| 4,386,912 A | 6/1983 | Nogase et al. | 433/228 |
| 4,457,818 A | 7/1984 | Denyer et al. | 204/159.19 |
| 4,525,256 A | 6/1985 | Martin | 204/159.18 |
| 4,558,120 A | 12/1985 | Tomalia et al. | 528/363 |
| 4,587,329 A | 5/1986 | Tomalia et al. | 528/363 |
| 4,674,980 A | 6/1987 | Ibsen et al. | 433/228.1 |
| 4,746,686 A | 5/1988 | Waller | 522/14 |
| 4,857,599 A | 8/1989 | Tomalia et al. | 525/259 |
| 4,952,241 A | 8/1990 | Reiners et al. | 106/35 |
| 5,274,064 A | 12/1993 | Sarkar | 528/25 |
| 5,308,886 A | 5/1994 | Masuhara et al. | 522/81 |
| 5,395,883 A | 3/1995 | Yates, III et al. | 525/89 |
| 5,418,301 A | 5/1995 | Hult et al. | 525/437 |
| 5,468,789 A | 11/1995 | Lewis et al. | 524/99 |
| 5,486,548 A | 1/1996 | Podszun et al. | 523/115 |
| 5,530,092 A | 6/1996 | Meijer et al. | 528/363 |
| 5,679,794 A | 10/1997 | Suhadolnik et al. | 546/186 |
| 5,767,170 A | 6/1998 | Ibsen et al. | 522/81 |
| 5,814,681 A | 9/1998 | Hino et al. | 523/113 |
| 5,834,118 A | 11/1998 | Ranby et al. | 428/482 |
| 5,847,020 A | 12/1998 | Ibsen et al. | 522/84 |
| 5,847,025 A | 12/1998 | Moszner et al. | 523/116 |
| 5,886,064 A | 3/1999 | Rheinberger et al. | 523/116 |
| 5,914,379 A | 6/1999 | Sutoris et al. | 526/204 |
| 5,955,514 A * | 9/1999 | Huang et al. | 523/118 |
| 5,969,000 A | 10/1999 | Yang et al. | 523/116 |
| 5,985,958 A | 11/1999 | Moszner et al. | 524/83 |
| 6,025,114 A | 2/2000 | Popat et al. | 430/284.1 |
| 6,030,606 A | 2/2000 | Holmes | 424/49 |
| 6,031,016 A | 2/2000 | Ibsen et al. | 522/79 |
| 6,121,344 A | 9/2000 | Angeletakis et al. | 523/116 |
| 6,136,885 A | 10/2000 | Rusin et al. | 523/116 |
| 6,184,339 B1 | 2/2001 | Stansbury et al. | 528/407 |

FOREIGN PATENT DOCUMENTS

| | | |
|---|---|---|
| DE | 22 11 128 | 9/1973 |
| DE | 3 703 080 | 1/1988 |
| DE | 3 703 120 | 1/1988 |
| DE | 295 645 | 7/1990 |
| EP | 023 686 | 7/1980 |
| EP | 049 599 | 9/1981 |
| EP | 059 649 | 3/1982 |
| EP | 102 199 | 8/1983 |
| EP | 140 140 | 9/1984 |
| EP | 254 950 | 7/1987 |
| EP | 0 630 640 | 12/1994 |
| EP | 0 673 637 | 9/1995 |
| EP | 765 856 | 9/1995 |
| EP | 716 103 | 11/1995 |
| EP | 995 421 | 10/1999 |
| SU | 334 845 | 1/1984 |
| WO | 92/21314 | 12/1992 |
| WO | 93/12759 | 7/1993 |
| WO | 96/07688 | 3/1996 |
| WO | 97/02328 | 1/1997 |
| WO | 97/47272 | 12/1997 |

OTHER PUBLICATIONS

Standish et al; "Cure of Resin Based Restorative Materials; I. Self Cure Resins"; Australian Dental Journal; Apr. 1983; vol. 28; No. 2; pp. 82–86.

Cook et al; "Cure of Resin Based Restorative Materials; II. White Light Photopolymerizable Resins"; Australian Dental Journal; Oct. 1983; vol. 28; No. 5; pp. 307–311.

Standish et al; "Polymerization Kinetics of Resin–Based Restorative Materials"; Journal of Biomedical Materials Research; vol. 17, pp. 275–282 (1983).

Liso et al; "Analysis of the Leaching and Toxicity of New Amine Activators for the Curing of Acrylic Bone Cements and Composites"; Biomaterials 18 (1997) pp. 15–20; 1996 Elsevier Science Limited.

Kannurpatti et al; "Polymerization Behavior and Properties of networks Formed by Dimethacrylate Dental Resisn"; Division of Polymer Chemistry, Inc., American Chemical Society; vol. 38; No. 2; Sep. 1997; pp. 106–107.

Cook et al; "A Simple Method for the Measurement of Polumerixation Shrinkage Dental Composites"; Dental Materials 15 (1999); pp. 447–449.

NCBI National Library of Medicine; Br J Nutr Aug. 1998; 80 Suppl: S77–112; "Functional Food Science and Defence Against Reactive Oxidative Species"; 2 pgs.

(List continued on next page.)

Primary Examiner—Tae H. Yoon
(74) Attorney, Agent, or Firm—Douglas J. Hura; James B. Bieber

(57) ABSTRACT

Dental compositions comprising at least a polymerizable monomer and/or at least a polyaminoester that are prepared by reaction of bis- or polyacrylic esters and amines, pigments, organic and/or inorganic fillers, initiators and stabilizers.

2 Claims, No Drawings

OTHER PUBLICATIONS

NCBI National Library of Medicine; Crit Rev Food Sci Nutr 1994; 34(5–6): 47–97; "Antioxidants and Hormone–Mediated Health Benefits of Whole Grains"; 1 page.

NCBI National Library of Medicine; Santerre; Effect of Filler Content on the Profile of Released Biodegradtion Products in Micro–Filled bis–GMA/TEGDMA Dental Composite Resins; Biomaterials Oct. 1999; 20(20); 1897–908; 1 pg.

NCBI National Library of Medicine; Crit Rev Oral Biol Med 1996; 7(2): 172–9; Bioavailability of Components of Resin–Based Materials Which Are Applied to Teeth; 1 pg.

R.S. Davidson, J.W. Goodin, Eur. Polym. J. 18 (1982) pp. 597–606.

C. Dekker, Makromol. Chem. 180 (1979) pp. 2027–2030.

C.R. Morgan, A.D. Ketley, J. Radiat.Curing 7 (1980) pp. 10–13.

C.R. Morgan, F. Magnott, A.D. Ketley, J. Polym. Sci., Polym. Ed. 15 (1977) pp. 627–645.

G. Smets, Bull. Soc. Chim. Belges 71 (1962) pp. 857–858.

G. Oster, J. Amer. Chem. Soc. 79 (1957) pp. 595–598.

P. Ferruti et al., Polymer 26 (1985) pp. 1336–1348.

H.G. Elais, Makromolekule, Huttig & Wepf, Basel 1990, p. 555.

Do Thi Bich Loan, I.m. Panayotov, Eur. Polym. J. 32 (1996) pp. 957–962.

Japanese Patent Abstract; vol. 010, No. 262 (c–371) Sep. 6, 1986.

Ferruti P. et al; "Recent Results on Functional Polymers and Macromonomers of Interestas Biomaterials or for Biomaterial Modification".

Hill, I. R. C. et al; "in vivo cytotoxicity of poly(amidoamine)s: revelance to DNA delivery" BBA–General Subjects, Elsevier Science Publishers, NL, vol. 1427, No. 2; Apr. 19, 1999, pp. 161–174.

* cited by examiner

POLYAMINOESTER AND THEIR APPLICATION IN DENTAL COMPOSITIONS

RELATED APPLICATIONS

This patent claims the benefit of U.S. Provisional Application Serial No. 60/224,669 filed Aug. 11, 2000.

DESCRIPTION OF THE INVENTION

Dental compositions comprising at least a polymerizable monomer and/or at least a polyaminoester of formulas 1 to 6, pigments, organic and/or inorganic fillers, initiators and stabilizers.

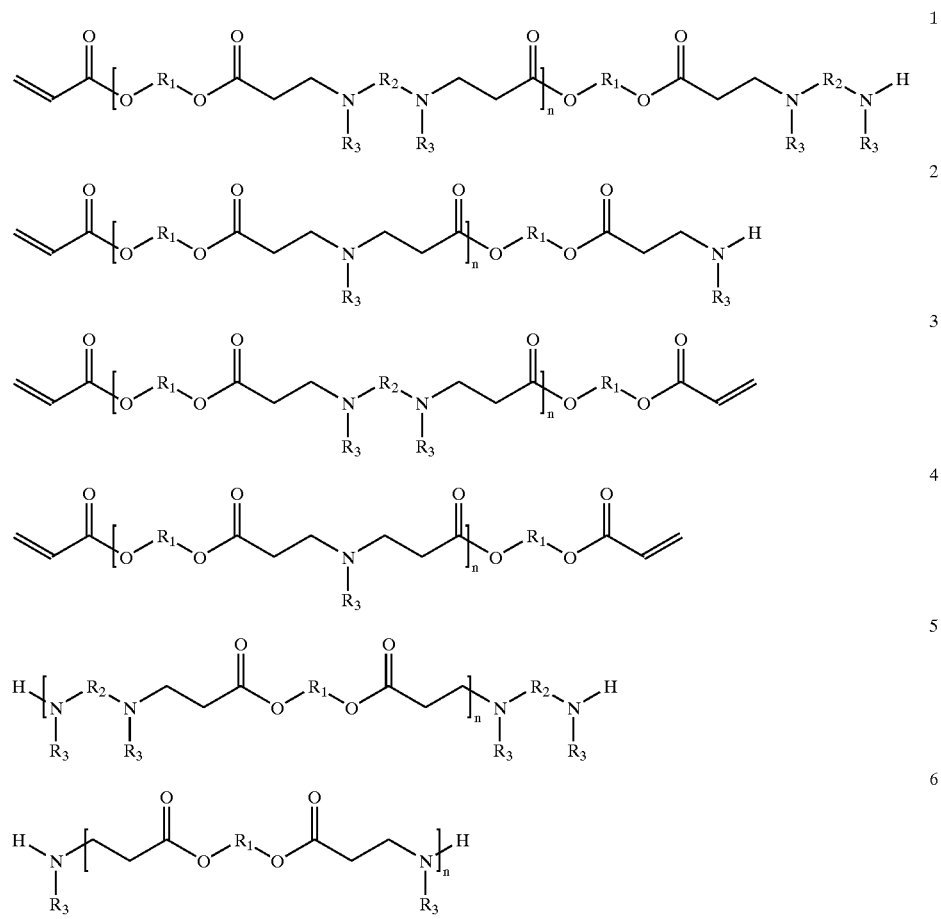

TECHNICAL BACKGROUND

Since some years, the addition polymerization of bisacrylamides and amines is well-known (P. Ferrutti et al., Polymer 26 (1985) 1336). Bisacrylamides are much more stable against hydrolysis compared to acrylic esters. The reaction of amines and esters lead to an transamidation reaction (H.-G. Elias, Makromoleküle, Hüttig & Wepf, Basel, 1990, p. 555).

Consequently, the assumption was that a reaction of acrylic esters and amines should lead to an cleavage of ester bonds. Therefore, the formation of addition polymers, prepolymers and macromonomers of amines and acrylic esters should be impossible.

Recently, oligoamido amines and oligoester amines based on antibiotics containing .beta-lactam rings were investigated (Panayotov, Eur. Polym. J. 32 (1996) 957–962). They were prepared by interaction between ampicillin and amoxicillin and methylenebisacrylamide, 1,4-diacryloylpiperazine and 1,3-propanediol diacrylate.

wherein $R_1$ denotes is a difunctional substituted or unsubstituted $C_1$ to $C_{18}$ alkylene, difunctional substituted or unsubstituted cycloalkylene, difunctional substituted or unsubstituted $C_5$ to $C_{18}$ arylene or heteroarylene, difunctional substituted or unsubstituted $C_5$ to $C_{18}$ alkylarylene or alkylheteroarylene, difunctional substituted or unsubstituted $C_7$ to $C_{30}$ alkylene arylene, $R_2$ denotes is a difunctional substituted or unsubstituted $C_1$ to $C_{18}$ alkylene, difunctional substituted or unsubstituted cycloalkylene, difunctional substituted or unsubstituted $C_5$ to $C_{18}$ arylene or heteroarylene, difunctional substituted or unsubstituted $C_5$ to $C_{18}$ alkylarylene or alkylheteroarylene, difunctional substituted or unsubstituted $C_7$ to $C_{30}$ alkylene arylene, $R_3$ denotes H or a substituted or unsubstituted $C_1$ to $C_{18}$ alkylene, substituted or unsubstituted cycloalkylene, substituted or unsubstituted $C_5$ to $C_{18}$ arylene or heteroarylene, substituted or unsubstituted $C_5$ to $C_{18}$ alkylarylene or alkylheteroarylene, substituted or unsubstituted $C_7$ to $C_{30}$ alkylene arylene, n is an integer.

Preferably the invented dental composition contains a polyaminoester that are characterized by the following formulas

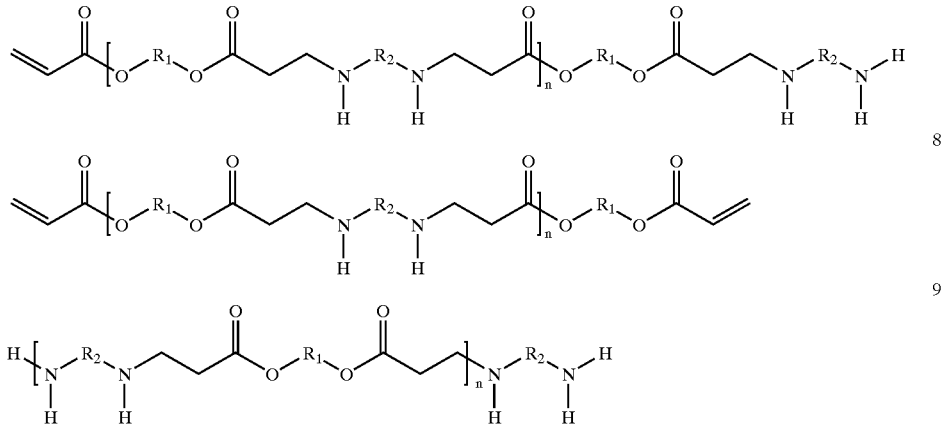

wherein
- $R_1$ denotes is a difunctional substituted or unsubstituted $C_1$ to $C_{18}$ alkylene, difunctional substituted or unsubstituted cycloalkylene, difunctional substituted or unsubstituted $C_5$ to $C_{18}$ arylene or heteroarylene, difunctional substituted or unsubstituted $C_5$ to $C_{18}$ alkylarylene or alkylheteroarylene, difunctional substituted or unsubstituted $C_7$ to $C_{30}$ alkylene arylene,
- $R_2$ denotes is a difunctional substituted or unsubstituted $C_1$ to $C_{18}$ alkylene, difunctional substituted or unsubstituted cycloalkylene, difunctional substituted or unsubstituted $C_5$ to $C_{18}$ arylene or heteroarylene, difunctional substituted or unsubstituted $C_5$ to $C_{18}$ alkylarylene or alkylheteroarylene, difunctional substituted or unsubstituted $C_7$ to $C_{30}$ alkylene arylene, and
- n is an integer.

Most preferably polyaminoesters are applied characterized by the following formulas decane, trimethylolpropane triacrylate or trimethylolpropane trimethacrylate, N,N'-dimethylaminoethyl methacrylate.

As fillers are applied inorganic or organic, reactive or nonreactive, surface modified or nonmodified glasses such as polymer granulate or a combination of organic and/or inorganic fillers, strontium alumo silicate glass, $La_2O_3$, $BiPO_4$, $ZrO_2$, $BaWO_4$, $CaWO_4$, $SrF_2$, $Bi_2O_3$.

Instead of primary monoamine and disecondary diamines the usage of polyamines is possible, too, leading to crosslinked polyaminoesters.

The invented dental composition preferably is applicable as root canal sealing material or as temporary crown & bridge material.

EXAMPLE 1

5.000 g (22.097 mmol) Hexamethylendiacrylate (Servo Delden) and 7.525 g (22.097 mmol) N,N'-Dibenzyl-5-nonandiamin-1,9 were mixed homogeneously and stirred at 60° C. for 4 days. After that time a complete conversion was found indicated by disappearance of the double bonds at 1635/1619 cm$^{-1}$.

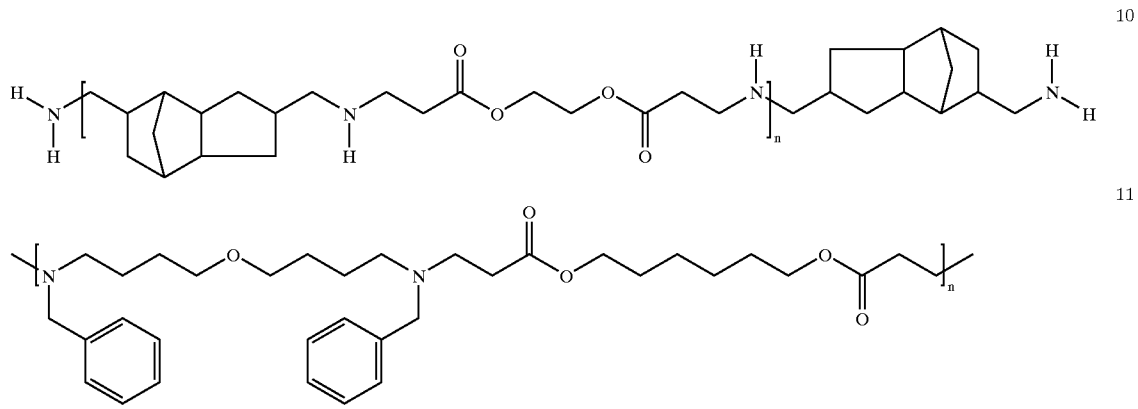

wherein n is an integer.

Said polymerizable monomer preferably are hydroxyethyl methacrylate, hydroxyethylacrylate, hydroxypropyl methacrylate, ethyleneglykol dimethacrylate, diethyleneglykol dimethacrylate, triethyleneglykol dimethacrylate, 3,(4),8,(9)-Dimethacryloyl-(oxymethyl)-tricyclo-5.2.1.0$^{2,6}$ Yield: 12.525 g (100% of th.)
$(C_{34}H_{50}N_2O_5)_n$, $(566.8)_n$
$[\eta]=8.57$ ml/g (Viscosity in THF solution)
IR: 2920/2865 ($CH_2$), 1735 (CO)
$M_n$ (GPC)=2225 (4661) g/mol
$M_w$ (GPC)=9398 (10200) g/mol

EXAMPLE 2

20.000 g (88.39 mmol) Hexamethylendiacrylate (Servo Delden) and 15.719 g (106.07 mmol) 3,6-Dioxaoctandiamin-1,8 (Fluka) were mixed homogeneously and stirred at room temperature for 1.5 hours. After that time a complete conversion was found indicated by disappearance of the double bonds at 1635/1619 cm$^{-1}$.

Yield: 35.719 g (100% of th.)

$(C_{18}H_{34}N_2O_6)_n$, $(347.5)_n$

η=4.73±0.05 Pa*s (dynamic viscosity measured using Bohlin CS50 rheometer)

IR: 3325 (NH), 2920/2865 (CH$_2$), 1735 (CO)

$^{13}$C-NMR (CDCl$_3$): 172.6/172.4 (6), 73.4 (2); 70.5/70.2 (3); 64.2 (7), 49.8 (1) 45.0 (4), 41.7 (4), 34.8 (5), 28.4 (8), 25.5 (9)

IR: 3325 (NH), 2920/2865 (CH$_2$), 1735 (CO)

EXAMPLE 3

10.000 g (58.77 mmol) Ethylene glycol diacrylate and 14.125 g (58.77 mmol) N,N'-Dibenzylethylenediamine were mixed homogeneously and stirred at room temperature for 40 hours at 60° C. After that time a complete conversion was found indicated by disappearance of the double bonds at 1635/1619 cm$^{-1}$.

Yield: 24.125 g (100% of th.)

η=1557±17 Pa*s (dynamic viscosity measured using Bohlin CS50 rheometer)

[η]=9.176 ml/g (viscosity in THF solution)

$M_n$ (GPC) =1575 g/mol

EXAMPLE 4

10.000 g (58.77 mmol) Ethylene glykol diacrylate and 20.012 g (58.77 mmol) N,N'-Dibenzyl-5-oxanonane diamine-1,9 were mixed homogeneously and stirred at room temperature for 40 hours at 60° C. After that time a complete conversion was found indicated by disappearance of the double bonds at 1635/1619 cm$^{-1}$.

Yield: 30.012 g (100% of th.)

η=188.8±1.3 Pa*s (dynamic viscosity measured using Bohlin CS50 rheometer)

[η]=10.051 ml/g (viscosity in THF solution)

$M_n$ (GPC)=4281 g/mol $M_w$ (GPC)=12110 g/mol $(C_{30}H_{42}N_2O_5)_n$, $(510.7)_n$

IR: 3060/3026/2943/2860/2802 (CH$_2$), 1740/1731 (CO)

$^{13}$C NMR (CDCl$_3$): 49.1 (1), 32.4 (2), 172.3 (3), 62.1 (4), 53.2 (5), 58.2 (6), 139.5 (7), 128.0 (8), 127.9 (9), 126.7 (10), 27.5 (11), 23.5 (12)

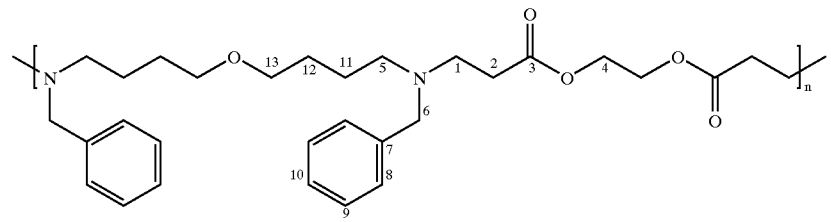

$M_w$ (GPC) =10060 g/mol $(C_{24}H_{32}N_2O_4)_n$, $(410.5)_n$

IR: 3060/3028; 2953/2816 (CH$_2$), 1743 (CO)

$^{13}$C NMR (CDCl$_3$): 49.7 (1), 32.4 (2), 172.6 (3), 621.0 (4), 51.5 (5), 58.6 (6), 139.2 (7), 128.6 (8), 128.0 (9), 126.8 (10)

EXAMPLE 5

10.000 g (58.77 mmol) Ethylene glykol diacrylate and 11.420 g (58.77 mmol) N,N'-Dibenzyl-4,4'-dicyclohexylmethane were mixed homogeneously and stirred at room temperature for 40 hours at 60° C. After that time a complete conversion was found indicated by disappearance of the double bonds at 1635/1619 cm$^{-1}$.

Yield: 21.420 g (100% of th.)

IR: 3060/3026/2943/2860/2802 (CH$_2$), 17401/1731 (CO)

EXAMPLE 6

10.000 g (58.77 mmol) Ethylene glykol diacrylate and 5.710 g (29.384 mmol) 3, (4),8, (9)-Bis(aminomethyl)-tricyclo-5.2.1.0 $^{2,6}$ decane were mixed homogeneously and stirred at room temperature for 2 hours at room temperature. After that time a complete conversion was found indicated by disappearance of the double bonds at 1635/1619 cm$^{-1}$.

Yield: 15.710 g (100% of th.)

η=Pa*s (dynamic viscosity measured using Bohlin CS50 rheometer)

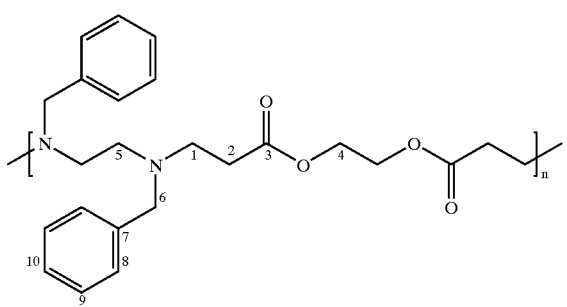

$(C_{28}H_{42}N_2O_8)_n$, $(534.7)_n$

IR: 3445/3332 (NH), 2947/2875/2821(CH$_2$), 1729 (CO); 1637/1619 (C=C)

EXAMPLE 7

10.000 g (58.77 mmol) Ethylene glykol diacrylate and 22.840 5.710 g (117.54 mmol) 3, (4),8, (9)-Bis (aminomethyl)-tricyclo-5.2.1.0 $^{2,6}$ decane were mixed homogeneously and stirred at room temperature for 2 hours at room temperature. After that time a complete conversion was found indicated by disappearance of the double bonds at 1635/1619 cm$^{-1}$.

Yield: 32.840 g (100% of th.)

η=218800±1990 Pa*s (dynamic viscosity measured using Bohlin CS50 rheometer)

$(C_{32}H_{54}N_4O_4)_n$, $(558.8)_n$

IR: 3373/3286 (NH), 2960/2888 (CH$_2$), 1743/1731 (CO)

$^{13}$C NMR (CDCl$_3$): 47.5 (1), 34.3/34.7 (2), 172.9 (3), 66.0 (4), 55.3 (5), signals of (6) to (15) between 24.5 and 63.5 ppm

EXAMPLE 8

To 10.000 g (58.77 mmol) Ethylene glykol diacrylate dissolved in 50 ml THF were slowly added at 0 to 5° C. under stirring a solution of 8.709 g (58.77 mmol) 3,6-Dioxaoctane diamine-1,8 in 50 ml THF. After adding the amine the solution was stirred at room temperature for 1.5 hours. After that time a complete conversion was found due to the disappearance of the double bonds at 1635/1619 cm$^{-1}$. Then the solvent was removed and the addition polymer was dried in vacuum.

Yield: 18.709 g (100% of th.)

η=Pa*s (dynamic viscosity measured using Bohlin CS50 rheometer)

$(C_{14}H_{26}N_2O_6)_n$, $(318.4)_n$

IR: 3373/3286 (NH), 2960/2888 (CH$_2$), 1743/1731 (CO)

Application Example 1 (Dental Root Canal Sealer)

Paste A 8.404 g (37.14 mmol) Hexamethylendiacrylate (Servo Delden), 25.968 g CaWO$_4$, 6.492 g ZrO$_2$ and 0.325 g aerosil were mixed homogeneously.

Paste B 7.217 g (37.14 mmol) 3, (4),8, (9)-Bis(aminomethyl)-tricyclo-5.2.1.0 $^{2,6}$ decane, 28.867 g CaWO$_4$, 7.217 g ZrO$_2$ and 0.722 g aerosil were mixed homogeneously.

Dental Root Canal Sealer

Immediately before use 0.214 g of Paste A and 0.200 g of Paste B were mixed homogeneously. The setting time of the root canal sealing material is 30 minutes. The radiopacity of 12.8 mm/mm Al.

Application Example 2 (Dental Root Canal Sealer)

Paste A 2.5213 g (11.14 mmol) Hexamethylendiacrylate (Servo Delden), 12.9298 g CaWO$_4$, 3.2325 g ZrO$_2$ and 0.0385 g aerosil were mixed homogeneously.

Paste B 0.801 g (5.29 mmol) 1-Aminoadamantane, 1.802 g (5.29 mmol) N,N'-Dibenzyl-5-oxanonandiamin-1,9, 0.103 g (0.53 mmol) 3, (4),8, (9)-Bis(aminomethyl)-tricyclo-5.2.1.0 $^{2,6}$ decane, 10.411 g CaWO$_4$, 2.603 g ZrO$_2$ and 0.315 g aerosil were mixed homogeneously.

Dental Root Canal Sealer

Immediately before use 0.173 g of Paste A and 0.200 g of Paste B were mixed homogeneously. The setting time of the root canal sealing material is 30 minutes. The radiopacity of 13.8 mm/mm Al.

We claim:

1. A dental composition comprising a polymerizable monomer, a polyaminoester, a pigment, a filler, an initiator and a stabilizer wherein said polyaminoester has a formula selected from

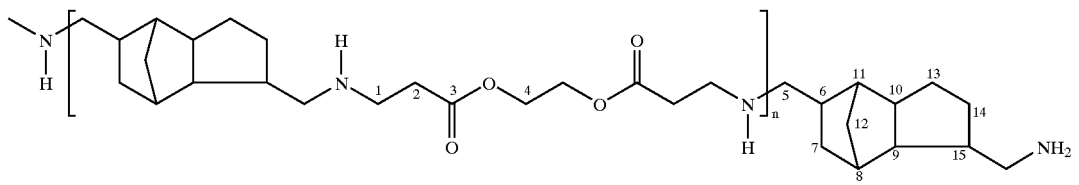

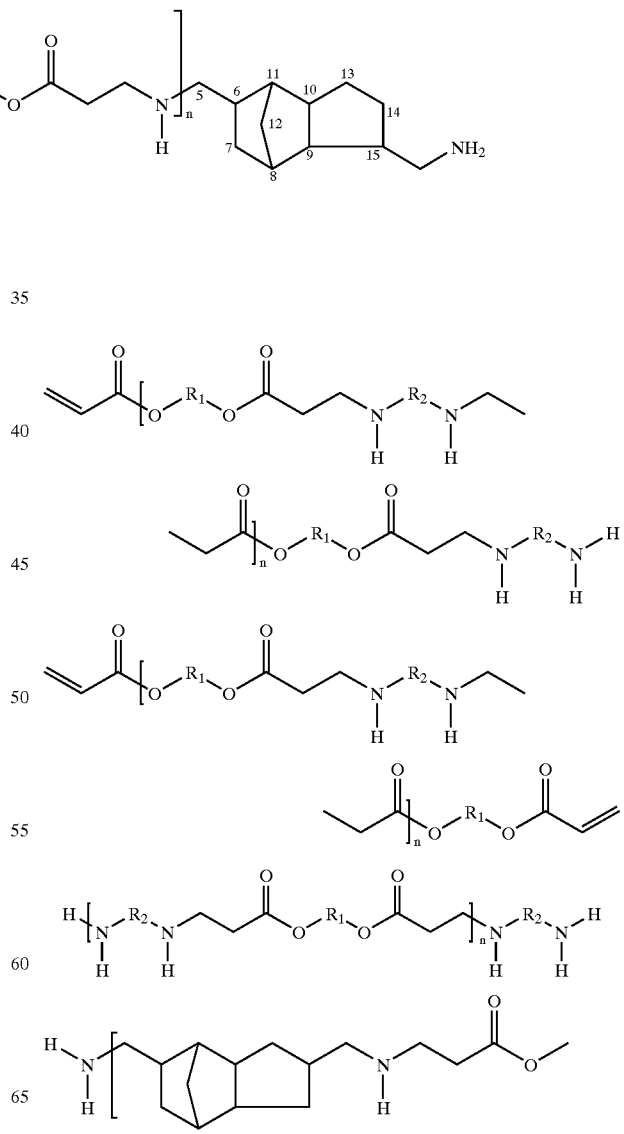

-continued

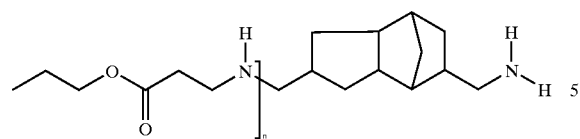

and

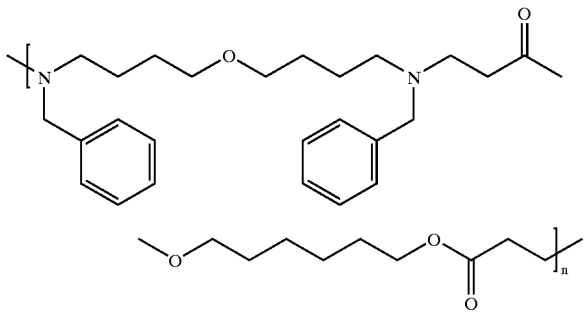

wherein $R_1$ denotes is a difunctional $C_1$ to $C_{18}$ alkylene, difunctional cycloalkylene, difunctional $C_5$ to $C_{18}$ arylene or heteroarylene, difunctional $C_5$ to $C_{18}$ alkylarylene or alkylheteroarylene, difunctional $C_7$ to $C_{30}$ alkylene arylene;

$R_2$ denotes is a difunctional $C_1$ to $C_{18}$ alkylene, difunctional cycloalkylene, difunctional $C_5$ to $C_{18}$ arylene or heteroarylene, difunctional $C_5$ to $C_{18}$ alkylarylene or alkylheteroarylene, difunctional $C_7$ to $C_{30}$ alkylene arylene; and, n is an integer.

2. Dental compositions comprising a polymerizable monomer and a polyaminoester selected from formulas 1 to 6, pigments, organic and/or inorganic fillers, initiators and stabilizers; wherein said polyaminoester has the formula selected from

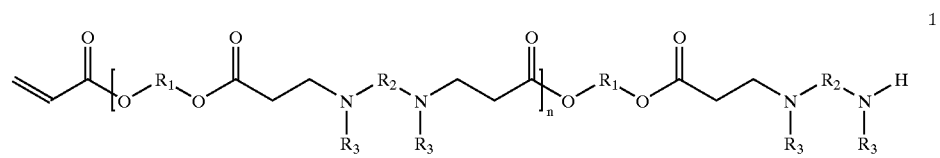

1

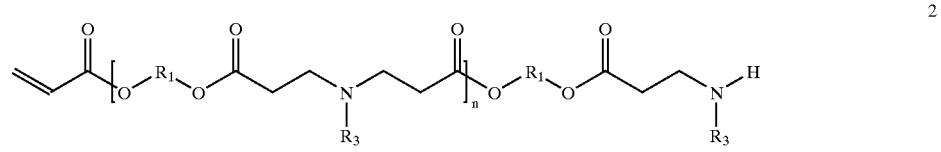

2

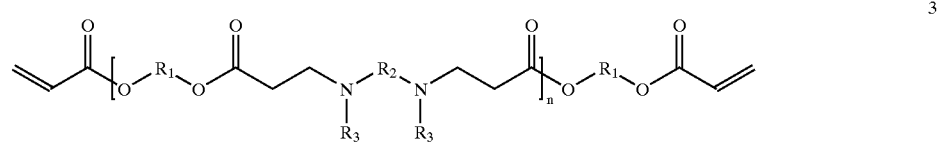

3

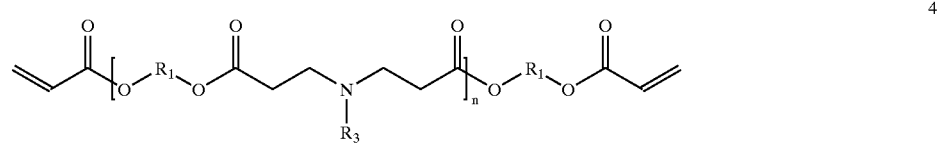

4

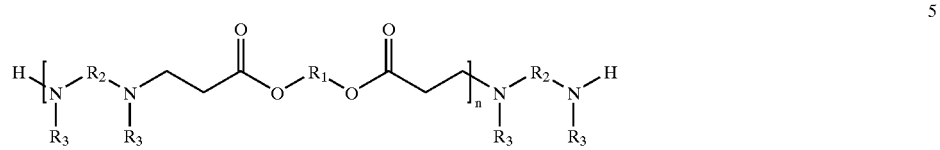

5 and

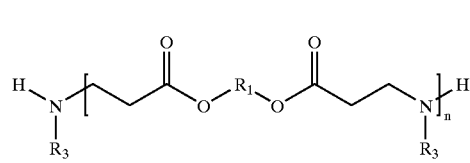

6 wherein
- $R_1$ denotes is a difunctional $C_1$ to $C_{18}$ alkylene, difunctional cycloalkylene, difunctional $C_5$ to $C_{18}$ arylene or heteroarylene, difunctional $C_5$ to $C_{18}$ alkylarylene or alkylheteroarylene, difunctional $C_7$ to $C_{30}$ alkylene arylene,
- $R_2$ denotes is a difunctional $C_1$ to $C_{18}$ alkylene, difunctional cycloalkylene, difunctional $C_5$ to $C_{18}$ arylene or heteroarylene, difunctional $C_5$ to $C_{18}$ alkylarylene or alkylheteroarylene, difunctional $C_7$ to $C_{30}$ alkylene arylene,
- $R_3$ denotes H or a $C_1$ to $C_{18}$ alkylene, cycloalkylene, $C_5$ to $C_{18}$ arylene or heteroarylene $C_5$ to $C_{18}$, alkylarylene or alkylheteroarylene, $C_7$ to $C_{30}$ alkylene arylene, and
- n is an integer; wherein said polyaminoesters are copolymerized with monomers that are usable for step-growth polymerization, with di- or polyepoxides or di- or polyisocyanates.

* * * * *